United States Patent [19]

Ingram et al.

[11] Patent Number: 5,955,444
[45] Date of Patent: Sep. 21, 1999

[54] METHOD OF INHIBITING ABNORMAL TAU HYPER PHOSPHORYLATION IN A CELL

[75] Inventors: Vernon M. Ingram, Cambridge, Mass.; Hanno M. Roder, Wupportal II, Germany

[73] Assignee: Massachusetts Institute of Technology, Cambridge, Mass.

[21] Appl. No.: 08/480,793

[22] Filed: Jun. 7, 1995

Related U.S. Application Data

[60] Division of application No. 07/912,293, Jul. 10, 1992, abandoned, which is a continuation-in-part of application No. 07/742,880, Aug. 9, 1991, abandoned.

[51] Int. Cl.[6] .................................................. A01N 31/70
[52] U.S. Cl. ................................................. 514/47; 514/46
[58] Field of Search ....................... 435/15, 7.21; 514/46, 514/47, 2, 313, 453, 468, 510, 691, 729, 739, 766; 424/130.1, 146.1; 530/387.1, 388.2, 388.1, 389.1

[56] References Cited

U.S. PATENT DOCUMENTS 5,385,915   1/1995   Buxbabun et al. .

*Primary Examiner*—Paula K. Hutzell
*Assistant Examiner*—Patricia A. Duffy
*Attorney, Agent, or Firm*—Wolf, Greenfield & Sacks, P.c.

[57] ABSTRACT

Novel TAU/neurofilament protein kinases, PK40 and PK36, are essentially purified and characterized. Novel immunoassays relating to the kinases and inhibitors for the kinases also are provided. Finally, DNA sequences encoding the kinases and cell lines relating to the kinases are provided. Methods of inhibiting abnormal tau HYPER PHOSPHORYLATION activity in a cell by contacting a cell with an inhibitor that binds to an ATP binding site of PK40, in an amount sufficient to inhibit said phosphorylating activity which is characteristic of abnormal tau HYPERPHOSPHORYLATION in Alzheimer's Disease is also provided.

3 Claims, 1 Drawing Sheet

Fig. 1

METHOD OF INHIBITING ABNORMAL TAU HYPER PHOSPHORYLATION IN A CELL

This application is a division of application Ser. No. 07/912,293 filed Jul. 10, 1992, now abandoned, which is a continuation-in-part of application Ser. No. 07/742,880, filed Aug. 9, 1991, now abandoned the entire contents of which are incorporated herein by reference.

This invention relates to novel TAU/neurofilament protein kinases, DNA sequences therefor and cell lines relating thereto, as well as inhibitors of the kinases and immunoassays relating to the kinases.

BACKGROUND OF THE INVENTION

Neurofilaments (NF), the intermediate filaments (IF) specific for neurons, are an assembly of three subunits of apparent Mr on SDS-PAGE of 68 kD, 160 kD and 200 kD, termed NF-L, NF-M and NF-H, respectively. All three subunits contain a highly conserved helical rod domain. The two heavier subunits also have extended C-terminal tail domains which are heavily phosphorylated. The cDNA-derived sequences of the two heavy NF-subunits have revealed the presence of 5, 12 and 40 Lys-Ser-Pro (Val,Ala, X) repeats in the C-terminal domains of rat NF-M, human NF-M and human NF-H, respectively (Napolitano et al., 1987; Myers et al., 1987 and Lees et al., 1988). These sequences form the epitopes of several phosphoepitope-specific anti-NF-mAbs (Lee et al., 1988). The physiological significance of NF and their phosphorylation is not very well understood yet (reviewed by Matus, 1988); correlative evidence suggests involvement in the regulation of axonal diameter (Hoffman et al., 1987; Pleasure et al., 1989). Electron microscopic studies in conjunction with antibody decoration (Hirokawa wt al., 1984) and biochemical evidence (Minami et al., 1983) favor NF-H as a component in interactions of the NF and microtubule networks. The phosphorylation status of NF and their ability to promote tubulin polymerization are correlated in vitro (Minami et al., 1985).

The existence of NF-kinase(s) not activated by common second messengers and some of their expected properties were postulated from in vivo phosphorylation studies on extruded axoplasm of the giant axons of the squid (Pant et al., 1978, 1986) and of Myxicola (Shecket et al., 1982). In vitro characterization of purified NF-kinases has focused so far on activities that copurify with the NF-cytoskeleton and can be dissociated under high salt conditions (Runge et al., 1981; Toru-Delbauffe et al., 1983). There is currently no evidence of second messenger dependence of any of these activities. From a mixture of such kinases one 67 kD activity has been purified to apparent homogeneity (Wible et al., 1989). This kinase prefers NF-H as a substrate, but only if not completely dephosphorylated. A cAMP-dependent kinase copurifying with microtubules has been shown to phosphorylate preferentially NF-M in NF-triplets (Leterrier et al., 1981). In no case are the stoichiometry or the sites of phosphorylation known and no shift of apparent Mr of NF-M and NF-H on SDS-PAGE has been demonstrated. Such a shift is expected after incorporation of phosphate in high stoichiometric ratios into the dephosphorylated subunits. A smaller than expected gel shift associated with a heterogeneous state of KSP-phosphorylation of NF-M is induced by uncharacterized kinases in mouse L cells transfected with a human NF-M clone (Pleasure et al., 1990).

A possible pathological role of aberrant NF-phosphorylation was considered when the anti-rat-NF mAb 07-5 (commercially available as SMI-34 from Sternberger-Meyer Immunochemicals of Jarretsville, Md., U.S.A.) was found to stain neurofibrillary tangles in brain tissue from Alzheimer's patients (Sternberger et al., 1985), but did not stain normal human brain tissue, except for cerebellar basket cell axons and certain motoneuron axons of patients 60 years of age (Blanchard & Ingram, 1989). On the other hand, there is a report that the localization of the SMI-34 epitope is exclusively perikaryonal, while most other mAbs reacting with NF-phosphoepitopes stain axons preferentially (Sternberger et al., 1983).

However, immunochemical evidence (Grundke-lqbal et al., 1986; Kosik et al., 1986; Wood et al., 1986; Nukina et al., 1987) concerning the crossreactivities of a series of mAbs with NFs, microtubule associated protein TAU and the main component of tangles and paired helical filaments (PHF) point to TAU as a major constituent of PHFs. This deduction is reinforced by the isolation from PHFs of TAU-derived peptides (Wischik et al,, 1988), while no NF-derived peptides (Kondo et al., 1988) were obtained. A number of anti-NF mAbs crossreacting with TAU, among them SMI-31 (commercially available from Sternberger-Meyer Immunochemical) and RT97, recognize the phosphorylated KSP-sequence repeat in NF proteins (Lee et al., 1988). PHFs react strongly with RT97, but only after prolonged treatment with SDS, suggesting the presence of this phosphorylated epitope in PHF in a nonperipheral location (Rasool et al., 1984). Several lines of evidence indicate an abnormal level or an abnormal site of phosphorylation in the C-terminal portion of the TAU molecule in Alzheimer's Disease (AD) (Grundke-lqbal et al., 1986; Kondo et al., 1988; Iqbal et al., 1989). If an abnormally phosphorylated form of TAU is responsible for or involved in the development of neurological conditions characterized by PHFs in neurofibrillary tangles, then it clearly would be extremely important to identify the factor(s) which cause that phosphorylation.

SUMMARY OF THE INVENTION

The invention provides preparations containing isolated, essentially pure, nonskeletal-associated kinases, the kinases capable of phosphorylating dephosphorylated NF-M to an extent sufficient to cause a shift on SDS-PAGE of the apparent $M_r$ of dephosphorylated NF-M toward that of native NF-M. The kinases further are capable of phosphorylating both dephosphorylated and native Tau and are capable of phosphorylating and reconstituting phosphoepitopes on completely dephosphorylated NF-triplet or purified dephosphorylated NF-M. The kinases also are inhibited by excess ATP.

One kinase, PK40, has an apparent molecular weight of 40 kD and is capable of phosphorylating completely dephosphorylated NF-M to an extent sufficient to cause a complete shift of apparent molecular weight from that of completely dephosphorylated NF-M to that of native NF-M. This kinase also is capable of causing a complete shift for TAU and a partial shift for NF-H. It in particular can phosphorylate TAU to an extent that mimicks the alterations characteristic of human TAU proteins extracted from PHFS. It further can phosphorylate both KSP sites of TAU and can abolish the TAU-1 epitope.

Another kinase, PK36 has an apparent molecular weight of 36 kD and is capable of phosphorylating completely dephosphorylated NF-M to an extent sufficient to cause at least a partial shift of apparent molecular weight from that of completely dephosphorylated NF-M toward that of native NF-M.

According to another aspect of the invention, novel assays are provided. One assay involves a method for detecting a mammalian kinase. A fraction of biological material derived from a mammal is prepared, it being unknown whether the fraction contains the kinase of interest. The fraction is substantially free of epitopes characteristic of a phosphorylated protein and reactive with a test antibody. The fraction is contacted with a dephosphorylated protein free of the epitope under conditions so as to permit the phosphorylation of the protein if the kinase is present. The fraction then is tested for the presence of the epitope using the test antibody. Preferably the fraction is contacted with a completely dephosphorylated neuroprotein. The presence of the epitope can be detected using an antibody reactive with an epitope correlated with phosphorylated neuroproteins such as SMI-31 antibody or SMI-34 antibody, and reagents may be employed to produce a color in the presence of an immunoprecipitate complex between the antibodies and the epitope. The color produced then may be measured as a quantitative measure of the presence of the complex.

In a similar immunoassay, the fraction of biological material derived from a mammal is prepared, being unknown whether the fraction contains the kinase of interest. The fraction is substantially free of epitopes that are characteristic of a protein in a particular state of phosphoralation and that are reactive with the test antibody. (Particular state of phosphoralation includes completely dephosphoralated.) The fraction is contacted with a protein that is characterized by the epitope under conditions so as to permit the phosphoralation of the protein if the mammalian kinase is present. The presence of the epitope that is tested for using the antibody. If the epitope has dissappeared, then the kinase is present. Examples of useful antibodies include SMI-33 and TAU-1. Preferred substrates include neuroproteins that are reactive with the foregoing antibodies, such as, for example, the phosphoralated TAU.

Another novel immunoassay according to the invention involves use of an antibody that is reactive with an epitope characteristic of a particular state of phosphoralation of a protein, and use of the protein in a state of phosphoralation that does not bind to the antibody. Such immunoassays may be in the form of a kit including a container with the first container containing the antibody and the second container containing the protein. Preferrably the protein is a neuroprotein and most preferrably the protein is desphosphoralated TAU.

Yet another novel immunoassay according to the invention employs dephosphorylated NF. Preferred embodiments involve assays utilizing completely dephosphorylated NF-triplet, completely dephosphorylated NF-M and completely dephosphorylated NF-H.

According to another aspect of the invention, antibodies to the novel kinase of the invention are provided. Monoclonal and polyclonal antibodies capable of binding to and, preferably selectively specific for PK40 and PK36 are provided. Most preferably the antibodies are capable of inhibiting the kinase activity of either PK40 or PK36. The antibodies may be used among other things for detecting the presence of PK40 or PK36.

The invention also provides methods for inhibiting neuroprotein phosphorylation activity in a cell by introducing into a cell an inhibitor of PK40 or PK36 in an amount sufficient to inhibit the phosphorylation activity of the PK40 or PK36. Preferred inhibitors include fragments of substrates of PK40 or PK36, antibodies selectively specific for PK40 or PK36 and ATP or analogs of ATP. Most preferably the inhibitor is administered in an amount sufficient to prevent the formation of neurofilament tangles.

According to still another aspect of the invention, vectors are provided containing oligonucleotides encoding PK40 or unique fragments thereof and PK36 or unique fragments thereof. Likewise, cell lines are provided that are transformed or transfected with an oligonucleotide encoding PK40 or a unique fragment thereof or PK 36 or a unique fragment thereof. Products of the cell line also are provided.

These and other features of the invention are described in greater detail below in connection with the detailed description of the preferred embodiments.

DETAILED DESCRIPTION OF THE PREFERRED EMBODIMENT

The invention in one aspect involves the identification of novel kinases, PK40 and PK36. PK40 and PK36 have been isolated from bovine brain as described in Example 4 and are essentially pure. By "essentially pure" it is meant that at least 40% of the material in a preparation is the kinase of interest. Preferably the kinase represents at least 80%, and most preferably the kinase represents at least 90%, of the material in the preparation. In any event, the preparations of the invention are sufficiently pure so as to permit amino acid sequencing by conventional methods, and further, can be made sufficiently pure to permit the generation and identification of antibodies to the kinases of interest. PK40 and PK36 have apparent molecular weights ($M_r$) of 40 kD and 36 kD on SDS-PAGE, respectively.

A unique characteristic of PK40 is its slight shift (C<1) in apparent molecular weight during the purification procedures of the invention. This is believed to be due to phosphorylation of PK40 during purification. The kinases are noncytoskeletal-associated. "By noncytoskeletal-associated it is meant that the kinase does not co-purify with the NF-cytoskeleton under high-salt extraction conditions." PK40, but not PK36, normally is isolated in a tyrosine phosphorylated form.

The kinases are capable of phosphorylating a variety of dephosphorylated native substrates. The native substrates have characteristic mobilities on SDS-PAGE which change when the substrates are dephosphorylated. Treatment of these dephosphorylated substrates with the kinases of the invention under conditions permitting phosphorylation of the substrates, may result in a mobility shift on SDS-PAGE of the apparent $M_r$ of the dephosphorylated substrate toward that of the native substrate, depending upon the particular substrate and kinase selected, and the conditions applied. A "shift" is any detectable change in mobility. By "complete shift" it is meant that the mobility of the previously dephosphorylated substrate, after treatment with the kinase of the invention, is the same as that of the native substrate. A "partial shift" means that the mobility has moved between that of the dephosphorylated substrate and that of the native substrate. "No shift" means no detectable change in mobility after treatment of the dephosphorylated substrate with the kinase of the invention.

PK40 is capable of phosphorylating completely-dephosphorylated NF-M (cdNF-M) so as to cause a complete shift on SDS-PAGE of the apparent $M_r$ of the cdNF-M to that of native NF-M. PK40 causes a partial shift of completely-dephosphorylated NF-H (cdNF-H). PK40 further is capable of causing a complete shift of completely-dephosphorylated native bovine TAU or pure human TAU isoform expressed in *E.coli* from the clone Htau 40 (Goedert et al. 1989). In this regard, under saturation phosphorylation conditions, PK40 causes a change in the isoform pattern that closely resembles the pattern of human TAU proteins extracted from PHF. This and other pattern changes are discussed in greater detail below. It also phosphorylates both KSP sites of TAU and abolishes the TAU 1 epitope.

PK36 is capable of phosphorylating cdNF-M so as to cause at least a partial shift on SDS-PAGE of the apparent $M_r$ of the cdNF-M to that of native NF-M. It also can cause a partial shift with respect to TAU.

Neither kinase is activated by the usual second messengers, i.e., small molecules (such as cAMP, cGMP, Calcium, $Ca^+$ Phosphatidyl Serine and Ca/CAM) that are produced inside the cell when the outside of the cell membrane receives a signal or stimulus, such as a peptide hormone.

The ATP dependence and inhibition of the activities of PK40 and PK36 were determined as described in Example 6. The apparent $K_m$ value for ATP of PK40 is $93^{\pm}12 \mu M$ and of PK36 is $50 \mu M$. These values reflect a requirement for relatively high ATP concentrations. Both kinases, however, are strongly inhibited by an excess of ATP, i.e., when ATP is in relatively small excess over $Mg^{2+}$. In addition, PK36, but not PK40, is inhibited by the Walsh inhibitor.

Identification of these novel kinases was made possible by the employment of a novel kinase immunoassay described herein. This immunoassay required NF proteins devoid of immunoreactivity with mAbs SMI-31 and SMI-34, in that the assay measures kinase activity specific for epitopes recognized by these antibodies, i.e., the repeated phosphorylated KSP sequences. In order to be devoid of such immunoreactivity, the NF proteins were completely dephosphorylated as described in Example 1. Thus, by "completely dephosphorylated", it is meant nonreactive with SMI-31 and SMI-34 antibodies. With such dephosphorylated substrates, it is possible to assay for kinase activity i.e., the rephosphorylation of the KSP sequences, by measuring the reappearance of immunoreactivity with SMI-31 and SMI-34. Thus, the completely-dephosphorylated NF proteins were incubated with different ammonium sulfate fractions from bovine brain supernatants, and reconstitution of the SMI-31 and SMI-34 epitopes was assayed in the different fractions, as described in Example 2.

A colorimetric immunoassay also described in Example 2, can be used to quantitatively measure levels of phosphorylating activity. In such an assay, the presence of the epitopes characteristic of phosphorylated NF proteins is tested using reagents that produce a color in the presence of an immunoprecipitate complex between antibodies such as SMI-31 or SMI-34 and the phosphorylated NF proteins. The amount of color produced is determined, thus providing a quantitative measurement of the amount of complex formed. Such a measurement correlates with the KSP-specific phosphorylating activity present in the sample tested. Again, completely-dephosphorylated neuroprotein can be used as a substrate, although there are instances that do not necessarily require completely-dephosphorylated material as a substrate.

The invention also pertains to the nucleic acids encoding the human kinases corresponding to bovine PK40 and PK36, and to a method for cloning DNA sequences encoding the human kinases. The purified bovine kinases are sequenced as described in Example 11. With this sequence information, oligonucleotide probes are constructed and used to identify the gene encoding the human kinase in a cDNA library. Due to degeneracy of the genetic code, most amino acids are represented by more than one codon. Therefore, in order to increase the proportion of codons on the probe that actually correspond to the codons in the genome, the amino acid sequence chosen from the bovine kinase that is used to synthesize the corresponding oligonucleotide probe will be from a region that has a minimal amount of degeneracy. Specifically, a radiolabeled synthetic oligonucleotide hybridization probe corresponding to the least degenerate codon sequence of a peptide sequence for each of kinase PK40 and PK36 is prepared and used to screen a CDNA library from human cells as described in Example 12. For PK40 it is preferred to use codon sequences corresponding to the unique fragments. Sequence I.D. Nos. 1 and 2.

Clones are obtained whose codon order matches the amino acid sequence of each of the kinases. From overlapping partial clones, a full-length cDNA sequence for each of the human kinases, which correspond to bovine PK40 and PK36, is thus identified, and recombinant vector molecules containing the total cDNA sequences are obtained. Such a cloning method can be utilized because each of the corresponding human kinases is encoded by an oligonucleotide with substantial homology to either bovine PK40 or PK36. Thus, there is sufficient homology such that the human cDNA is capable of being identified by the hybridization technology described herein.

A vector containing an oligonucleotide means a vector containing the cDNA sequence, but not necessarily expressing it. For expression of the cDNA sequence, it must be operably linked to a eukaryotic or prokaryotic expression control DNA sequence. Such recombinant molecules are easily prepared and identified by one of ordinary skill in the art using routine skill and without undue experimentation.

Cells transformed or transfected with these recombinant vector molecules are capable of expressing the human kinase, or fragments thereof. Alternatively, the human kinases can be isolated according to the methods described in the Examples that were used for isolating bovine PK40 and PK36.

The human PK40 and PK36 kinases are inhibited by excess ATP, phosphorylate dephosphorylated neurofilament and TAU proteins, and in particular, phosphorylate KSP sequences in these proteins. Human kinases herein mean those nonskeletal-associated kinases identified as described in this invention, including human PK40 and human PK36. Except for the Examples, as used herein and in the claims, PK40 and PK36 mean mammalian PK40 and PK36, naturally occurring and cloned. In the Examples, unless specifically referred to otherwise, PK40 and PK36 mean bovine PK40 and PK36. By human PK40 and PK36, is meant the human kinases corresponding to bovine PK40 and PK36.

According to another aspect of the invention, antibodies, both polyclonal and monoclonal, can be raised against the kinases of the invention, and then, if desired, selected on the basis of their ability to inhibit the phosphorylating activity of the kinases. Monoclonal antibodies are obtained by the method described by Milstein and Kohler. Such a procedure involves injecting an animal with an immunogen, removing cells from the animal's spleen and fusing them with myeloma cells to form a hybrid cell, called a hybridoma, that reproduces in vitro. The population of hybridomas is screened and individual clones are isolated, each of which secretes a single antibody species to a specific antigenic site on the immunogen. The monoclonal antibodies are useful for detecting the presence or absence of the PK40 or PK36 kinases. In addition, the monoclonal or polyclonal antibodies are useful as inhibitors of the PK40 and PK36 kinases.

Because PK40 has sequence homology with ERK kinases, it will be understood that certain preferred antibodies will be selected so as not to react with such ERK kinases. Preparing such antibodies is well within the level of skill in the art.

The invention also involves the identification, of inhibitors of PK40 and/or PK36. An inhibitor of PK40 or PK36 is a molecule that is capable of binding to PK40 or PK36 in a manner so as to inhibit the phosphorylating activity of PK40 or PK36. This invention discloses that PK40 and PK36 are strongly inhibited by an excess of ATP. Other inhibitors may be identified by those of ordinary skill in the art using the assays as described herein, e.g., adding the putative inhibitor to the kinase and subjecting the mixture to the quantitative colorimetric immunoassay described in Example 2. Thus, various analogs and conjugates of ATP may be screened for their ability to inhibit the phosphorylating activity of PK40 or PK36. Examples of analogs are readily available in the literature and can be accessed using various data-bases, including full-text patent data-bases. The inhibitors thus can resemble the molecular structure of ATP, especially in the distribution of charged groups. The inhibitors can be modified to enable them to enter neurons in a variety of ways. For example, the charged groups of ATP analogs can be modified by esterification by analogy with dibutyryl-cyclic-AMP.

Tens of thousands of putative inhibitors may be screened, first in mixtures containing, for example, 1000 candidates, and then, after inhibition by a mixture is established, in submixtures containing, for example, 100, then 10, and then one inhibitor. Other inhibitors may include, but are not limited to, KSP binding site proteins, or proteins which bind to one of the kinases of this invention, e.g., substrates, fragments of substrate, antibodies, fragments of antibodies, and peptides such as single chain antibody constructs or structural analogs of any of these. A substrate of PK40 or PK36 is a protein that is acted upon by PK40 and/or PK36 in vivo. An inhibiting fragment of a substrate of PK40 and/or PK36 as used herein is a peptide that is a structural analog of at least a portion of the substrate and that is capable of binding to PK40 and/or PK36, so as to titrate out the phosphorylating activity of PK40 and/or PK36 for the native substrate. Such fragments may be identified and prepared by cleaving substrates of PK40 and/or PK36, e.g., neurofilament or TAU protein, and testing the ability of the fragments produced thereby to interfere with the phosphorylating activity of the kinase for native substrate. Alternatively, structural analogs of the PK40 or PK36 substrates may be prepared which contain at least one KSP site and are resistant to degradation by cytoplasmic, proteolytic enzymes. Such fragments are easily prepared and identified by one of ordinary skill in the art using routine skill and without undue experimentation. For example, they can be prepared from known sequence information of substrates of the kinases of the invention.

A use of this invention is to administer to a cell an inhibitor of one of the kinases of the invention. This can act to reduce the phosphorylation activity in the cell and also to reduce or prevent the formation of paired helical filaments or tangles. This permits the analysis, for example, of the contribution of such phosphorylation activity to cell maintenance as well as to neurocellular states characteristic of neurodegenerative disease and aging.

A therapeutic use of this invention is to administer to a subject in need of such treatment an inhibitor of one of the kinases of this invention in order to treat neurodegenerative conditions characteristic of Alzheimer's disease and normal aging. Such an inhibitor can reduce the formation of paired helical filaments.

The inhibitor is administered to a subject in a therapeutically acceptable amount. The term "subject" is intended to include mammals. The term "therapeutically acceptable amount" is that amount which is capable of ameliorating or delaying progression of the diseased or degenerative condition in the subject. A therapeutically acceptable amount can be determined on an individual basis and will be based, at least in part, on consideration of the subject's size, severity of symptoms to be treated, results sought, and the specific inhibitor used. A therapeutically acceptable amount can be determined by one of ordinary skill in the art employing such factors and using no more than routine experimentation.

As discussed herein, inhibitors include, but are not limited to, ATP, analogs of ATP, KSP binding site proteins, or proteins which bind to one of the kinases of this invention, e.g., substrates, fragments of substrate, antibodies, fragments of antibodies, and peptides such as single chain antibody constructs.

Administration of the inhibitor of this invention may be made by any method which allows the inhibitor to reach the target cells. Typical methods include oral, rectal, peritoneal, subcutaneous, intravenous and topical administration of the inhibitor. Other delivery systems can include sustained release delivery systems. Preferred sustained release delivery systems are those which can provide for release of the inhibitor of the invention in sustained release pellets or capsules. Many types of sustained release delivery systems are available. These include, but are not limited to: (a) erosional systems in which the inhibitor is contained in a form within a matrix, found in U.S. Pat. Nos. 4,452,775 (Kent) and 4,667,014 (Nestor et al.); and (b) diffusional systems in which an active component permeates at a controlled rate through a polymer, found in U.S. Pat. Nos. 3,832,252 (Higuchi et al.) and 3,854,480 (Zaffaroni). In addition, a pump-based hardware delivery system can be used, some of which are adapted for implantation directly into the brain.

A particular problem which must be overcome for those systems which deliver inhibitor via the bloodstream is to cross the blood-brain barrier, which controls the exchange of materials between the plasma and the central nervous system. Many substances are unable to pass through this barrier. One way to accomplish transport of the inhibitor across the blood-brain barrier is to couple the inhibitor to a secondary molecule, a carrier, which is either a peptide or a non-proteinaceous moiety. The carrier is selected such that it is able to penetrate the blood-brain barrier. Examples of carriers are fatty acids, inositol, cholesterol, and glucose derivatives. Alternatively, the carrier can be a compound which enters the brain through a specific transport system in brain endothelial cells, such as transport systems for transferring insulin, or insulin-like growth factors I and II. This combination of inhibitor and carrier is called a prodrug. Upon entering the central nervous system, the prodrug may remain intact or the chemical linkage between the carrier and inhibitor may be hydrolyzed, thereby separating the carrier from the inhibitor.

An alternative method for transporting the inhibitor across the blood-brain barrier is to use liposomes. Liposomes are single or multi-compartmented bodies obtained when lipids are dispersed in aqueous suspension. The walls or membranes are composed of a continuous lipid bilayer which enclose an inner aqueous space. Such vesicles can be used to encapsulate and deliver therapeutic agents. International Patent No. WO 91/04014 (Collins et al.) describes a liposome delivery system in which the therapeutic agent is encapsulated within the liposome, and the outside layer of the liposome has added to it molecules that normally are transported across the blood-brain barrier. Such liposomes can target endogenous brain transport systems that transport specific ligands across the blood-brain barrier, including but not limited to, transferring insulin, and insulin-like growth factors I and II. Alternatively, antibodies to brain endothelial cell receptors for such ligands can be added to the outer liposome layer. U.S. Pat. No. 4,704,355 (Bernstein) also describes methods for coupling antibodies to liposomes. In addition, U.S. Pat. No. 4,704,355 describes preparing liposomes which encapsulate ATP.

The invention also describes a novel assay that can be used as a diagnostic test for early Alzheimer's disease. The assay measures the level of neuroprotein phosphorylation activity in a human cell by human kinases corresponding to PK40 and PK36. Skin fibroblasts are grown in vitro from a normal and from a test subject. Varying concentrations of an uncoupler of oxidative phosphorylation from ATP production are added to the skin fibroblasts and the presence of immunological epitopes that are correlated with phosphorylated neuroproteins are determined. Fibroblasts from Alzheimer's patients show this effect at lower concentrations of uncoupling agent than fibroblasts from normal subjects. The appearance of such epitopes will indicate the release from inhibition of kinases PK40 and PK36.

Antibodies selectively specific for PK40 or PK36 also can be used to evaluate the level of neuroprotein phosphorylation activity, by quantifying the amount of PK40 or PK36 present in a tissue sample. It is believed that diseased states will be characterized by a higher level of kinase present.

EXAMPLE 1

The novel kinase immunoassays required NF proteins devoid of immunoreactivity with mAbs SMI-31 and SMI-34. These immunoassays measure kinase activity specific for these epitopes, i.e., the repeated KSP sequences. Such specificity was required because crude brain extracts contain a very large number of protein kinases. In order to be devoid of such immunoreactivity, the NF proteins must be completely dephosphorylated. NF-triplet protein and individual NF-subunits were prepared, and subsequently dephosphorylated, as follows.

NF-triplet protein was prepared by one of two methods: "native" or "reconstituted." The preparation of "native" NF-triplet was a modification of previously described procedures (Tokutake et al., 1983; Lee et al., 1987). A freshly obtained bovine spinal cord (100–150 g, Arena & Sons, Hopkinton, Mass.) was desheathed, minced with a razor blade and left for 2 hours in 3 l of 10 mM Tris, pH 7.0, 50 mM NaCl, 2 mM EGTA, 1 mM DTT, 0.1 mM PMSF at 4° C. for swelling. The supernatant was decanted and the swollen tissue was homogenized for 1 minute in 200 ml of a similar buffer containing 150 mM NaCl (isotonic buffer) with an Ultra-Turax at ⅔ speed. After 15 minutes centrifugation at 12,000×g the precipitate was twice rehomogenized in 200 ml isotonic buffer for 1 minute at full speed. Supernatants of the centrifugations were-combined and made 0.85M in sucrose by adding solid sucrose (1 mole/l). Centrifugation at 100,000×g for 4 hours yielded about 200 mg of gelatinous precipitate which was dissolved (aided by slow Ultra Turax homogenization) in 100 ml adsorption buffer: 10 mM potassium phosphate, pH 7.4, 8M urea (deionized for 1–2 hours over mixed bed ion exchanger AG 501-X8 (D), Bio-Rad), 0.5% β-mercapto-ethanol (β-ME). NFs were absorbed by shaking this solution for 10 minutes at 4° C. with hydroxyapatite (HTP, 40 g, dry weight, Bio-Rad), preequilibrated in adsorption buffer. The adsorbent was sedimented for 10 minutes at 15,000×g and washed (10 minutes each) subsequently with 100 ml adsorption buffer, 3×85 ml 130 mM $KPO_4$, pH 7.0, 8M urea, 0.5% β-ME and once each with 50 ml 300 mM and 250 mM $KPO_4$, pH 7.0, 8M Urea, 0.5% β-ME. The supernatants of the latter two washes contained the bulk amount of NF-L, NF-M and NF-H and were combined for reconstitution of the NF-triplet by dialysis into 3 changes of 1 liter of 10 mM MES, pH 6.8, 100 mM NaCl, 1 mM MgCl$_2$ and 1 mM EGTA. After 30 minutes of incubation at 37° C. and centrifugation for 6 hours at 120,000×g, 40–60 mg of NF-triplet proteins were obtained. The gelatinous precipitate was rehomogenized in 40% glycerol with a glass-teflon homogenizer to form suspensions of 2.5–3 mg/ml and stored at −20° C.

For separation of the individual NF-subunits a previously described procedure (Tokutake, 1984) was modified. The native NF-triplet precipitate was taken up (0.5–1 ml/mg NF protein) in 10 mM sodium phosphate, pH 6.8, 6M urea, 0.5% β-ME (starting buffer), centrifuged at 100,000×g for 1 hour and loaded onto a 40×1.5 cm DEAE-Sephacel column (Pharmacia). NF subunits were eluted at room temperature with 600 ml of a linear gradient formed by starting buffer and 400 mM sodium phosphate, pH 6.8, 6M urea, 0.5% β-ME at 10–15 ml/hour. Fractions were collected (120 fractions, 5 ml each) and fractions 41–48, 71–80 and 85–94 were pooled; these contained pure NF-H, NF-M, and NF-L, respectively, according-to analysis by SDS-PAGE. The three fractions were concentrated to 2–3 ml by vacuum dialysis and dialysed into water. NF-L was obtained as a clear gelatinous precipitate after centrifugation for 1 hour at 100,000×g; NF-M and NF-H were precipitated by ammonium sulfate. For storage at −20° C. the pure subunits were homogenized (NF-L) or dissolved (NF-M, NF-H) in 40% glycerol to form stock concentrations of about 1 mg/ml of protein. Alternatively, NF-subunits were separated by FPLC on a Mono Q 5/5 column (Karlsson et al., 1987).

The "reconstituted" NF-triplet was reconstituted from the three purified subunits after recombination of the appropriate column fractions, in a manner similar to that described above for reconstitution of "native" NF-triplet protein.

Dephosphorylation of NF-triplet was accomplished with *E. coli* alkaline phosphatase. One ml (2.5–3 mg) of NF-triplet stock solution was incubated for 5 days at 37° C. with 10 units (about 400 μg) *E. coli* alkaline phosphatase (type III-N, Sigma Chemicals) in a total volume of 2 ml, containing 50 mM Tris pH 8.5, 100 mM NaCl, 0.5 mM MGSO$_4$, 0.5 mM ZnSO$_4$, 1 mM PMSF and 5 μg leupeptin. The NF triplet protein was separated from the phosphatase by centrifugation for 1 hour at 100,000×g, 4° C. The pellet was washed twice by rehomogenization in 2 ml water. The final pellet (yield 40–50%) was resuspended by a glass-teflon homogenizer in 40% glycerol to form a stock solution of about 0.5 mg/ml, stored at −20° C. Dephosphorylated NF-triplet tended to aggregate over several weeks of storage. After analytical SDS-PAGE of dephosphorylation reactions, phosphatase and accompanying impurities were removed by subjecting the gel for 6 hours to a "Western-blot electrophoresis" in an SDS-free buffer prior to staining.

Dephosphorylation of subunit NF-M was accomplished by incubating NF-M (0.5 g) with 2 units (80 μg) *E. coli* alkaline phosphatase for 5 days in a total volume of 1 ml under the same buffer conditions as used for the NF-triplet. The phosphatase was removed by gel filtration of the mixture on a 50×1N5 cm Sephadex G200 column (50–120 μm, 10 ml/hr flow rate), equilibrated with 10 mM BisTris, pH 7.0, 100 mM NaCl. Fractions were analyzed by SDS-PAGE. NF-M containing fractions around the exclusion volume were pooled (4 ml), dialyzed into water,- concentrated in a SpeedVac and stored at −20° C. as a 0.3 mg/ml stock solution containing 40% glycerol. The yield was 270 μg (54%).

Dephosphorylation of subunit NF-H was accomplished by incubating NF-H (1.05 mg) with 120 μg calf intestinal alkaline phosphatase for 6 days at 37° C. in a total volume of 1.5 ml containing 50 mM Tris, pH 8.5, 1 mM MgSO$_4$, 1 mM PMSF and 15 μg leupeptin. Separation from the phosphatase, concentration and storage were as described for NF-M. The yield was 700 μg (67%).

The dephosphorylation reactions for both NF-subunits were monitored by spotting 1–1.5 μg of NF-protein on nitrocellulose. Blocking, staining with SMI-31 and SMI-34 and development of the blots were performed as described for Immuno-dotblot assays.

The shift of apparent $M_r$ on SDS-PAGE (1.5 mm gels (Laemmli, 1970), 7.5% acrylamide, accompanying dephosphorylation of NF-M and NF-H in the "native" triplet was virtually completed within minutes. Five days of incubation, however, was necessary to completely abolish the SMI-31 and SMI-34 immunoreactivity and create substrates suitable for the immunoassays of the invention. The phosphatase was removed quantitatively by repeated sedimentation of the dephosphorylated triplet. Dephosphorylation of the NF-M and NF-H subunits in the NF-triplet which had been "reconstituted" from FPLC-purified subunits, occurred much more slowly as monitored by gel shift, removal of SMI-31 reactivity and generation of the SMI-33 epitope. mAb SMI-33 (Sternberger—Meyer Immunochemicals) is specific for the non-phosphorylated KSP sequence, Lee et al., 1988. Loss of SMI-31 reactivity was not complete even after five days of incubation.

FPLC-purified NF-M, but not FPLC-purified NF-H, was dephosphorylated with *E. coli* alkaline phosphatase so as to be unreactive to SMI-31 and SMI-34 under conditions similar to those used for the NF-triplet. For the FPLC-purified NF-H, the shift of apparent $M_r$ on SDS-PAGE and the removal of SMI-31 and SMI-34 immunoreactivity remained incomplete even after five days of incubation with high concentrations of *E. coli* alkaline phosphatase. The immunoreactivity of FPLC-purified NF-H with SMI-31 and SMI-34, however, was removed with calf intestinal alkaline phosphatase (special molecular biology grade, Boehringer Mannheim Biochemicals) after five days of incubation. NF-M was completely dephosphorylated with either phosphatase. The phosphatases were removed by gel filtration. Heat treatment and freezing of the NF were avoided because the proteins tended to aggregate.

EXAMPLE 2

The preferred method for the immunoassay for detecting KSP-phosphorylating kinases is as follows. Dephosphorylated NF-triplet protein was incubated with the 35–45% ammonium sulfate fraction of the brain supernatant (see section B.). Immuno-dotblot assays were performed in 50 mM HEPES, pH 7.0, 2 mM MgCl$_2$, 1 mM ATP, 2 mM DTT in a total volume of 30 μl with 5 μg of dephosphorylated native NF-triplet or 1.2 μg of dephosphorylated pure subunits NF-M or NF-H as substrates together with a control assay lacking NFs. After incubation at 37° C. for 18 hours, assays were diluted to 100 μl with 10 mM PBS, pH 7.2, and aliquots of 50 μl were spotted on nitrocellulose (0.22 μm, Schleicher and Schüll). Blots were blocked by 1 hour incubation with 3% BSA in 10 mM PBS, pH 7.2, and washed once in 0.5% Triton-X100/10 mM PBS. Antibodies were diluted in sterile 10 mM PBS, pH 7.2, 0.5% Triton-X100, 10% fetal calf serum. Blots were incubated with SMI mAbs for at least 2 hours. The blots were then washed five times. Mouse mAbs were detected by reaction with horseradish-peroxidase-linked goat-anti-mouse antibody (Cappel Co.) in 1:200 dilution and by staining with 0.05% 4-chloro-1-naphthol (Sigma) and 0.05% $H_2O_2$ in 50 mM TBS, pH 7.5, 33% ethanol for 5–20 minutes. All incubations and washes were at room temperature. Incubations were sealed in plastic bags with 50 μl of solution/cm² membrane.

The SMI-31 and SMI-34 epitopes were reconstituted. The activity was NF-specific, since control immunoassays lacking dephosphorylated NF-triplet were negative. These site specific kinase immunoassays, while only semiquantitative, nevertheless allowed for the estimation of some of the properties of the kinases while still in crude form.

The foregoing procedure involved parameters that were optimized as follows. Immuno-dotblot-assays (0.5 mM $Mg^{2+}$, 0.5 mM ATP) were performed using various ammonium sulfate fractions of whole brain supernatant to determine the fraction containing the desired activity. The control assays did not contain NF proteins. A 35–45% fraction was found to contain the strongest activity for reconstituting SMI-31 and SMI-34 epitopes. This activity was NF-specific, since the corresponding control immunoassay which lacked dephosphorylated native NF-triplet was almost negative for this fraction. An additional less permanent NF-specific activity was detected in the 40–55% and 55–70% AS-fractions of cytoskeletal extract with 0.8M KCl where the main NF-kinase activity had been expected.

The soluble nature of the kinases in the 35–45% fraction was confirmed when the activity did not cosediment under low salt conditions (10 mM HEPES Buffer pH7) after 15 minutes of incubation with the phosphorylated native NF-triplet at 37° C. or assembled cold solubilized microtubules according to the method of Shelanski et al (1973) [4M glycerol, 1 mM GTP, 37° C., 30 minutes], in the absence or presence of 5 m Mg/ATP.

The optimal incubation time, pH and NaCl concentration for conducting the assay was determined using the 35–45% fraction. The assays were performed with 0.5 mM $Mg^{2+}$ (unless indicated otherwise). At an ATP concentration of 1 mM, an 18 hour incubation time was optimal; the assays for pH and NaCl were performed at the 18 hour incubation time. The assay responses were optimal at pH 7.0, low salt conditions (50 mM or less; 10, 20, 50, 75 and 100 mM tested) and 1 mM ATP.

Immuno-dotblot-assays were conducted to determine the optimal $Mg^{2+}$ and ATP concentrations using the SMI-31 and SMI-34 antibodies. The amount of enzyme-was varied as follows: 0.04, 0.09, 0.13, 0.18, 0.22, 0.33 and 0.44 micrograms of crude enzyme. Control assays were without NFs using 0.4 micrograms crude enzyme. $Mg^{2+}$ and ATP concentrations were at 1.0, 2.0, and 4.0 mM.

The optimal $Mg^{2+}$ and ATP concentrations were found to be 2 mM and 1 mM, respectively. ATP [5 mM] inhibited the kinase activity. $Mn^{2+}$ was about twice as effective as $Mg^{2+}$. GTP could not substitute for ATP. Concentrations of NaCl greater than 20 mM diminished the assay response. This effect was attributable to ionic strength rather than specifically to sodium or chloride ions, since the same decline was seen with $(NH_4)_2SO_4$ at comparable ionic strength.

Alternatively, a quantitative colorimetric immunoassay of PK40 and PK36 can be used. Such an assay measures binding of mAbs to dephosphorylated human or other specie neurofilaments, TAU protein, or recombinant TAU protein by kinases PK40 and PK36. The kinases PK40 and PK36, alone or together, were assayed by a quantitative ELISA-type assay based on the mAbs SMI-31, SMI-34 (Sternberger—Meyer Immunochemicals, Jarretsville, Md.) as primary antibody. The secondary antibody was horseradish-peroxidase-linked goat anti-mouse antibody (Cappel Co.), followed by color development with $H_2O_2$ and "ABTS" (2,2'-Azino-bis-(3-ethylbenzthiazoline-6-sulfonic acid).$2NH_4^+$), and color extraction and measurement. Different amounts of PK40 and/or PK36 were incubated with 6 μl 250 mM HEPES buffer, pH 7.0/10 mM MgS04, 1.2 μl 25 mM ATP and 40–160 ug of dephosphorylated bovine neurofilament triplet protein in a total volume of 30 μl. Incubation was for 18 hours at 37° C. and was followed by dilution to 150 μl with 10 mM PBS. Each assay (20 μl) was applied to a nitrocellulose membrane as a dot, the membrane was blocked with bovine serum albumin and individual dots were punched out. They were next incubated with SMI-31 mAb (1:500, 100 μl) for 6 hours at 25° C. Each dot was washed 5× with 1 ml of PBS containing Triton X-100. The second incubation was with the goat anti-mouse Ab, 1:200 for 6 hours at 25° C., followed by washing 5× with 1 ml PBS/Triton X-100. Color development was carried out by shaking each dot individually with a 0.1% ABTS in citrate pH 4.0/0.03% $H_2O_2$ at room temperature for 30 minutes. The reaction produced a soluble color in the supernatant which was measured at 415 nm.

EXAMPLE 3

An alternative method for assaying the phosphorylating activity of the kinases was by $^{32}P$ assays. Radioactive assays in the same buffer system as for immunoassays contained 5 μg of HTP-purified native NF-triplet as substrate (3 μg of substrate proteins other than-NFs) and 150–250 cpm/pmole gamma-$^{32}P$-ATP. Incubation times were 15 minutes at 37° C. for activities up to about 1 pmole/min/assay, since the assay responses were linear within these time intervals. Assays were stopped by cooling on ice, addition of 20 μl 25 mM EDTA and immediate transfer of the mixture onto glass filters (Whatman GF/A) wetted with 10% TCA/2% sodium pyrophosphate (PPA). The glass filters were washed twice for 1 hour and once for at least 3 hours in 10% TCA/2% PPA and finally in ethanol and were air-dried. Radioactivity was assessed by scintillation counting (Beckman LS 230) with 5 ml "Liquiscint" (National Diagnostics) for 20 minutes. Assays were routinely carried out in triplicate except for some duplicate assays in a few explicitly mentioned cases; a control assay lacking NFs was subtracted from the mean value.

A preferred substrate for this assay is TAU, prepared as described in the procedure of Example 9, below.

Assays to be analyzed on SDS-PAGE were stopped with an equivalent amount of sample buffer, boiled for 3 minutes and run on 7.5% gels. After staining with Coomassie Blue, destaining and drying on Whatman 3 MM paper, autoradiography was performed with a DuPont Cronex screen intensifier at −70° C. For quantitative measurements, radioactive bands of individual NF-subunits were cut out, placed in an Eppendorf vial immersed in 20 ml water and the Cerenkov radiation of the sample was counted. Counting efficiency was about 30%.

EXAMPLE 4

The method for purifying the kinases was optimized by exposing the 35–45% AS-fraction to a variety of chromatography media at 4° C. The activity as assayed using the SMI antibodies was lost in almost every case. These losses occurred even in the presence of 4M NaCl, which by itself did not affect enzyme survival in controlled experiments. (NaCl was added to prevent binding of the kinase or possible essential subunits to the chromatography media). It was discovered, however, that inclusion of Mg-ATP in the solution stabilized the activity on some media. In order of decreasing survival of activity, Sephadex Agarose, CM-Sepharose and quarternary ammonium ion exchangers were found to be useful chromatography media in the presence of MG-ATP.

The preferred method for purifying the KSP-phosphorylating kinases is as follows. Step I: A fresh bovine brain (350–450 g wet weight) was cleared from meninges and blood vessels and homogenized at 4° C. in 350 ml homogenization buffer (10 mM Bis Tris, pH 7.0, 150 mM NaCl, 2 mM EGTA, 1 mM DTT, 0.1 mM PMSF, 5 µg/ml leupeptin) with an UltraTurax or a Sorvall Omni-Mixer for 3 minutes. The pellet after centrifugation at 20,000×g for 20 minutes was extracted twice with 300 ml homogenization buffer. The turbid supernatants were clarified by centrifugation at 100,000×g for 1 hour. Solid ammonium sulfate was added slowly over about 1 hour while keeping the pH at 8.0–8.5 with ammonia. The precipitate obtained between 35% and 45% saturation was collected by centrifugation at 20,000×g for 20 minutes, redissolved in 20 ml 10 mM HEPES, pH 7.0, 1 mM MgCi$_2$, 1 mM EGTA and 1 mM DTT, and dialyzed extensively against this buffer to form a "crude enzyme" stock solution of about 20 mg/ml protein, which could be stored for several weeks at 4° C. with little loss of activity.

Step II: 20 ml of crude enzyme was dialyzed into CM-Sepharose starting buffer (5 mM magnesium acetate, 5 mM ATP, 1 mM DTT, 10% glycerol, 0.02% sodium azide, adjusted to pH 6.0 with BisTris) and loaded onto a 3×2.5 cm CM-Sepharose column equilibrated with starting buffer. The column was washed with 60 ml starting buffer at about 50 ml/hr, then the kinases were eluted in one step with 85 mM magnesium acetate, 5 mM ATP, 1 mM DTT, 10% glycerol, 0.02% sodium azide, pH 6.0 as a fraction of 15 ml volume.

Step III: The combined fractions of the CM-Sepharose chromatography containing the bulk of the activity were dialyzed into 10mM HEPES, pH 7, 1 mM EDTA and 1 mM DTT. The protein then was concentrated to about 3 ml in a SpeedVac and loaded onto a 95×2.5 cm column of Sephadex G200 Superfine (Pharmacia) and were eluted with a filtration buffer (48 mM BisTris, pH 7.0, 5 mM MgCl$_2$, 5 mM ATP, 1 mM DTT, 0.02% sodium azide). After elution of 155 ml at a flow rate of 1.5–2 ml/hr, fractions of 5 ml were collected.

Figure 1:
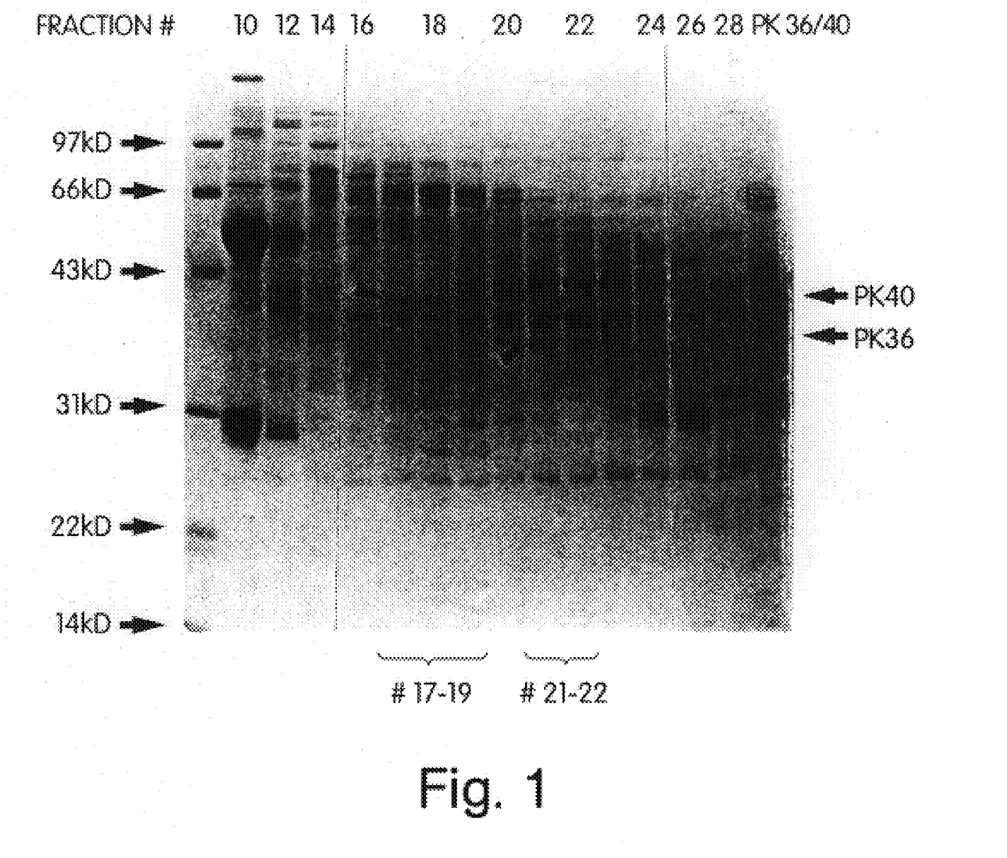
FIG. 1 is a photograph of a stained gel (12% SDS-PAGE) indicating the presence of PK36 and PK40.

The collected 5 ml fractions (10–28) were tested in immuno-dotblot-assays using SMI-31 and SMI-34 antibodies after 18 hours of incubation with NF-triplet. The fractions also were subjected to $^{32}$P-assays (30 minutes of incubation with NF-triplet) to test for the presence of kinase activity. The kinase activity eluted as a very broad peak (Fractions 14–23). No significant NF-specific phosphatase activity could be detected in the relevant kinase fractions by monitoring the liberation of phosphate under assay conditions from $^{32}$P-labeled dephosphorylated native NF-triplet, prepared by phosphorylation with partially purified NF-kinase. The fractions further were subjected to 12% SDS-PAGE gel electrophoresis. The PK40 and PK36 bands are identifiable (arrows, FIG. 1), with the PK40 being most prominent in fraction 17–19 and PK36 being most prominent in fractions 21 and 22. These fractions then were used in the assay method.

Step IV: Gel filtration fractions containing significant amounts of PK40 (17–19) and PK36 (21–22), according to SDS-PAGE analysis, were pooled, dialyzed into Mono Q starting buffer (20 mM Tris, pH 8.0, 20 mM MgCl$_2$, 5 mM ATP, 1 mM DTT, 0.02% sodium azide) and loaded on an HR 5/5 Mono Q FPLC-column (Pharmacia) equilibrated with starting buffer. Elution of PK40 at a flow rate of 1 ml/min started with 5 ml starting buffer followed by a linear gradient of 7 ml up to 60 mM MgCl$_2$, 7 ml isocratic elution at 60 mM MgCl$_2$ and finally a linear gradient up to 110 mM MgCl$_2$ formed with elution buffer (20 mM Tris, pH 8.0, 110 mM MgCl$_2$, 5 mM ATP, 1 mM DTT, 0.02% sodium azide). The gradient profile for PK36 was identical.

The various fractions were subjected to a variety of assays, including: a dotblot assay; a $^{32}$P-assay; and 12% SDS-PAGE gel electrophoresis. The activity within the fractions was demonstrated by the immuno-dotblot-assay and $^{32}$P-assay.

The activity of the PK40 fractions in the dotblot assay and $^{32}$P-assay were correlated with the particular fraction run on the SDS-PAGE gel and, importantly with the particular band revealed by the SDS-PAGE. The activity of the fractions correlated with presence of the gel electrophoresis 40 kD band. The assays revealed relatively prominent phosphorylation of NF-M and NF-H by PK40.

The activity of the PK36 fractions in the dotblot assay and $^{32}$P-assay correlated with the presence of the gel electrophoresis 36 kD band. The assays revealed relatively prominent phosphorylation of NF-M and NF-L by PK36.

Peak fractions of the NF-kinases (PK40: 11–12; PK36: 12–13) were pooled, dialyzed into storage buffer (20 mM BisTris, pH 7.0, 2 mM MgCl$_2$, 2 mM ATP, 1 mM DTT, 0.02% sodium azide) and concentrated about 10-fold in microconcentrators (Amicon 10) for storage purposes. The enzyme is stable when frozen. Activity was retained for several days at 4° C. and after 5 cycles of freeze-thawing with little loss. These pooled fractions were used in the preparations described below.

A relatively pure mix of PK36 and PK40 as used for the identification of 36 kD and 40 kD proteins as kinases was obtained after pooling of gel filtration fractions 16–23 and elution from Mono Q with an uninterrupted linear gradient of 17 ml from 20 mM to 110 mM $MgCl_2$.

To further confirm the identity of PK40 and PK36 as protein kinases, a highly enriched mixture of both kinases obtained as described (refer to above procedure for elution from Mono Q) was separated on polyacrylamide gels (PAGE) and the migration of both proteins was correlated with NF-kinase activity eluted from gel slices as follows:

The PK40/36 mixture was electrophoresed on a 10% PAGE containing SDS, 1 mM DTT and 5 mM MgATP. Gel slices of about 2 mm size were eluted overnight into small amounts of water. Aliquots of the supernatants were assessed for NF-kinase activity and activity by the $^{32}$P-assay followed by SDS-PAGE of NF and autoradiography. A comparatively weak NF-kinase activity correlated precisely with the presence of a 36 kD protein in the respective gel slices (as analyzed on 12% SDS-PAGE) while the 40 kD kinase apparently could not be renatured successfully from SDS.

To also prove the identity of the 40 kD protein as a kinase a similar experiment was performed whereby the PK40/36 mixture was separated on a non-denaturing 7.5% PAGE. In this case the 40 kD protein appeared as the dominating kinase very well correlated with activity.

Step V: The best preparations of PK40 were obtained after PK40 was run preparatively on nondenaturing 7.5% PAGE and was eluted from gel slices in an electro-eluter (model UEA, International Biotechnologies, New Haven, Conn.) in two consecutive 30 minute runs at 120 V and 4° C. into a trapping buffer consisting of 7.5M ammonium acetate, 10 mM Mg-ATP, 2 mM DTT and a trace of bromophenol blue. The elution buffer contained 25 mM Tris pH 8.3, 192 mM glycine, 2 mM Mg-ATP and 1 mM DTT. The kinase was dialyzed into a storage buffer of 20 mM BisTris pH 7.0, 2 mM Mg-ATP, 1 mM DTT, and concentrated about 10-fold in a microconcentrator (Amicon 10).

Table 1, below, details the enrichment of PK40 and PK36.

TABLE 1

Enrichment of PK40 and PK36 through various chromatographic steps

| Step | | spec. activity[c] | | total activity | | [mg] | |
|---|---|---|---|---|---|---|---|
| | | PK40 | PK36 | PK40 | PK36 | PK40 | PK36 |
| I) | AS-Fractionation | —[a] | — | — | — | 290 | |
| II) | CM-Sepharose | 0.55 | | 23.6 | | 43 | |
| III) | Sephadex G200 | 1.45 | 1.15 | 3.80 | 2.27 | 2.6 | 2.0 |
| IV) | Mono Q FPLC | 3.8 | 2.8 | 0.73 | 0.39 | 0.19 | 0.14 |
| V) | Prep. Gel-electrophoresis | 5.2 | —[b] | 0.67 | — | 0.13 | — |

[a]not determined. NF-specific activity too low against background.
[b]Electroelution of PK36 from a preparative SDS-gel was unsuccessful.
[c]nmoles 32P-P04 transferred/min/mg protein.
[d]nmoles 32P-P04 transferred/min.

The Mono Q fractions containing PK40 was further subjected to a two-dimensional SDS-PAGE gel separation procedure (O'Farrell procedure). A Western Blot assay was performed using a polyclonal anti-ERK antibody, Anti-rat MAP Kinase R2 (Upstate Biotechnology, Inc., N.Y. Cat #406-182). Western analysis revealed the presence of only one ERK protein, although three isoforms could be distinguished.

EXAMPLE 5

The substrate specificity of PK40 and PK36 was determined as follows. Among neuronal proteins tested, the specificity of PK40 for dephosphorylated NF-M was most striking. Other substrates were less efficient. The order of specificity was: dephosphorylated NF-M>>TAU>NF-M= NF-L>dephosphorylated NF-H>NF-H. PK36 had a lower specific activity than PK40, the substrate specificity being: NF-L=TAU=dephosphorylated NF-M>NF-M>>NF-H= dephosphorylated NF-H. Some microtubule-associated proteins were also good substrates for both kinases.

MAP2 in a crude microtubule-preparation was a substrate for PK40 and PK36 comparable to, or better than, TAU proteins, especially for PK40. MAP#2 is phosphorylated by both kinases above background level (PK40:2.5×; PK36:1.5×; determined by CERENKOV-counting). Background labeling of MAP2 was due to a second messenger independent activity intrinsic to cycled microtubules. Lysine-rich histone type III (calf thymus, Sigma Chemicals) was the most preferred substrate for both PK36 and PK40. This is a feature in stark contrast to all other known ERK kinases, which do not phosphorylate lysine-rich histone type III very well, and which phosphorylate microtubule associated proteins including TAU and MAP2 to a substantially greater extent than lysine-rich histone type eII. The acidic protein phosvitin (Sigma Chemicals) and tubulin (from calf brain, gift of Dr. F. Solomon, Dept. of Biology, MIT) were very poor substrates for either PK36 or PK40.

EXAMPLE 6

The ATP dependence and inhibition of the activities of PK40 and PK36 were determined at 2 mM $Mg^{2+}$ with soluble dephosphorylated NF-M as second substrate to avoid uncertainties arising from the aggregation state of NF-triplet in suspension. The optima were at 0.5–1 mM ATP for both kinases. Apparent $K_m$ values for ATP of both kinases were estimated from Woolf-Hanes plots (Dixon and Webb, 1979) for a range of ATP concentrations sufficiently below the onset of inhibition. Three determinations of the $K_m$ of PK40 at three different concentrations of the second substrate, NF-M, gave similar values (mean±S.D.:93±12 $\mu$M), indicating little influence of the concentration of NF-M on ATP-affinity of PK40. The apparent $K_m$ of PK36 was approximately 50 $\mu$M.

PK36 and particularly PK40 were strongly inhibited to 14% and 7%, respectively, of the control level in the presence of 5 mM ATP, amounting to 3 mM excess of free (uncomplexed) ATP over $Mg^{2+}$. In contrast, with excess $Mg^{2+}$ (5 mM over 1 mM ATP or 5 mM over 5 mM ATP), little or no inhibition was observed for PK40, while the activity of PK36 was significantly reduced.

The activity of the kinases was also reduced to 27% (PK40) and 40% (PK36) in the presence of 150 mM NaCl. Inhibition by the Walsh inhibitor was seen only for PK36, with an estimated $IC_{50}$ of 50 micromolar.

The foregoing is summarized in TABLE 2, below.

TABLE 2

Effect of sodium chloride, excess magnesium and ATP and of the Walsh inhibitor on the relative activity [%] of PK40 and PK36

|  | PK40[a] | PK36[a] |
|---|---|---|
| Control |  |  |
| 2 mM $Mg^2$ 1 mM ATP | 100[b] ± 6.9 | 100 ± 1.12 mM |
| 2 mM $Mg^2$ 5 mM ATP | 7.2 ± 6.9 | 14 ± 0.5 |
| 5 mM $Mg^2$ 1 mM ATP | 107 ± 3.5 | 40 ± 0.2 |
| 5 mM $Mg^2$ 5 mM ATP | 78 ± 7.1 | 38 ± 2.2 |
| NaCl 150 mM | 27 ± 1.8 | 40 ± 0.8 |
| Walsh Inhibitor [M] |  |  |
| 4.5 | 102 ± 5.3 | 103 ± 0.5 |
| 1.5 | 107 ± 3.7 | 87 ± 0.6 |
| 45 | 101 ± 1.1 | 58 ± 3.3 |

The values represent the mean of 3 assays (±S. D.); except for the Walsh inhibitor assays, which were carried out in duplicate.
[a]preparations of PK40: see Table 1, step V; preparations of PK36: see Table 1, step IV.
[b]All values represent relative activities in % of the control.

EXAMPLE 7

A comparison of the phosphorylating activity of PK40 and PK36 with other kinases was performed. Phosphorylation of the KSP sequence in dephosphorylated NF-triplet and dephosphorylated NF-M, using the SMI-31 immunoassay, i.e., measuring reconstitution of the SMI-epitopes, was achieved with a mixture of PK40 and PK36, but not with PKC, calcium/calmodulin dependent kinase II, cAMP-dependent kinase or second messenger-independent microtubule-associated kinase.

Phosphorylations with $Ca^{2+}$/calmodulin-dependent kinase II and protein kinase C were performed at 37° C. in 30 microliters of 50 mM HEPES, pH 7.5, 10 mM $Mg^{2+}$, 5 mM $Ca^{2+}$, 1 mM EGTA, 2 mM DTT, 1 mM ATP and 50 micrograms/milliliter calmodulin and phosphatidylserine, respectively, and 5 micrograms NF-triplet protein.

EXAMPLE 8

PK40 and PK36 induced mobility shifts of the heavy NF-subunits on SDS-PAGE and incorporated phosphate in high molar ratios. To determine the maximum number of phosphates incorporated into the heavy NF-subunits by PK40 and PK36 the purified activities of step V and step IV above were incubated in increasing concentrations with dephosphorylated NF-M and dephosphorylated NF-H. The stoichiometry of phosphorylation was determined by assuming that the correct molecular masses of NF-M and NF-H are 110 kD and 140 kD, respectively, as determined by Kaufmann et al. (1984), since SDS-PAGE considerably overestimates their $M_r$. The saturation phosphorylation of completely dephosphorylated NF-M and dephosphorylated NF-H by PK40 and PK36 was measured by assaying: (i) increasing amounts of enzyme activity measured against extent of phosphorylation in 18 hour assays as monitored by $^{32}P$-incorporation (mole $PO_4$ per mole NF-M); (ii) gel mobility shift on 7.5% SDS-PAGE; and (iii) SMI-31 and SMI-34 immunoassays. A mixture of PK40 and 36 also was tested.

PK40 incorporated up to 15 phosphate groups into NF-M which corresponds well to the number of phosphates found in isolated bovine NF-M (Wong et al., 1984) and induced a complete shift of the NF-M band on SDS-PAGE to the higher apparent $M_r$ of native NF-M. In contrast, only a partial shift of NF-H was achieved with a maximum of 7 phosphates introduced into a molecule with presumably about 40 KSP-sites. The phosphorylation of NF-M with PK36 appeared to be saturated at 10 moles phosphate/mole NF-M with a substantial gel mobility shift; however, the NF-M band remained diffuse, possibly due to a heterogeneous phosphorylation state. NF-H was not phosphorylated very well by PK36 and showed virtually no gel shift, in correlation with its poor substrate properties for PK36. Both kinases reconstituted the SMI-epitopes, but only weakly in the case of NF-H and PK36. The maximal phosphorylation of NF-M was not significantly higher with a mixture of the two kinases, indicating, that PK40 and PK36 might have a largely overlapping site-specificity on NF-M. After incorporation of 7–13 phosphates, NF-M had a gel mobility comparable to native NF-M. The SMI-immunoassay responses were correlated with the gel mobility shift, but did not respond at lower levels of phosphorylation, i.e., <5 moles $PO_4$/mole NF-M. The SMI-34 immuno-assay required a higher level of phosphorylation than the SMI-31 assay.

EXAMPLE 9

PK40 can induce a variety of changes in properties on both dephosphorylated and native TAU, which changes are of pathological interest.

To further confirm the effect of PK40 on TAU, bovine TAU was prepared. The procedure used is preferred as it can be carried out at 4° C. and results in a product that is free of phosphorylation that ordinarily would occur at higher temperatures.

TAU was prepared from fresh bovine brain according to Baudier et al. (1987). Briefly, 1 kg of brain tissue was homogenized in 1 liter of 100 mM potassium phosphate ($KPO_4$) buffer, pH 6.5, containing 2 mM each of EDTA and EGTA, 1 mM DTT, 0.1 mM PMSF and 5 mg/l each of aprotinin, leupeptin, antipain, antichymotrypsin and pepstatin A. Tissue debris was removed by centrifugation at 15,000×g and reextracted with 1 liter of $KPO_4$ buffer. Supernatants were made 45% in ammonium sulfate, the precipitate was collected after centrifugation at 20,000×g, rehomogenized and dialyzed extensively into $KPO_4$ buffer. The dialysate was adsorbed onto 8 g of preswollen CM-Sephadex, unbound material was removed by washing with $KPO_4$ buffer, and the TAU containing fraction was eluted with $KPO_4$/0.5M NaCl, pH 6.5. $HClO_4$ was added to 3%, precipitated material was removed by centrifugation and crude TAU in the Tris-neutralized supernatant was precipitated by 45% ammonium sulfate. The pellet was taken up in 5 ml water, dialyzed into 50 mM HEPES, 1 mM EDTA, 1 mM DTT, pH 6.9 (Mono S starting buffer). FPLC was performed on a 5/5 Mono S column (Pharmacia) with a linear gradient of 30 ml from 0 to 500 mM NaCl, whereby TAU eluted as a broad peak around 250 mM NaCl. TAU containing fractions were dialyzed into water and minor contaminating protease activities were destroyed by boiling for 5 minutes.

Dephosphorylated TAU protein was prepared by incubation of 300 µg native bovine TAU with 60 µg calf intestinal alkaline phosphatase (Boehringer Mannheim) and 20 µg E. coli alk. phoshpatase (Sigma type III-N) in 350 µl of 50 mM Tris, each 0.5 mM $MgSO_4$ and $ZnSO_4$, 0.1 mM PMSF, 10 µg/ml each of aprotinin, leupeptin, antipain, pepstatin and antichymotrypsin (all Sigma), pH 8.0, for 3 days at 37° C. Phosphates were removed by precipitation with 10 µl $HClO_4$ at room temperature. The supernatant was neutralized with Tris and dialyzed into water.

Gel mobility shifts of bovine and human TAU proteins induced by PK40 and PK36 phosphorylation was measured by incubating 10 µg of native or dephosphorylated bovine TAU (prepared according to the above alternative procedure) and 3 µg of bacterially expressed human TAU isoform hTau40 for 18 hr at 37° C. with about 25 pmole/min of PK40 or PK36. Analysis was performed by 10% SDS-PAGE and autoradiography.

Similar results were obtained with a pure 42 KD human TAU isoform expressed in E. coli from the clone Htau 40 (Goedert et al., 1989), kindly supplied as protein by Dr. E. M. Mandelkow. Under saturating conditions as described above, PK40 incorporated up to 14 phosphates into the 42 kD TAU isoform. PK36 induced a partial mobility shift in TAU protein, as in the case of NF-M.

Saturating phosphorylation by PK40 of dephosphorylated bovine TAU and of TAU native bovine TAU resulted in significantly reduced mobility on 10% SDS-PAGE as well as a characteristic change of the isoform patterns. The alterations produced in vitro result in a pattern that very closely resembles the pattern of human TAU-proteins extracted from PHF, whether native or dephosphorylated TAU was used. The shift in the pattern of human TAU proteins extracted from PHF relative to TAU from normal human brains is depicted clearly in (Goedert et al., 1992), which shift was shown to be entirely due to hyperphosphorylation.

On 10% SDS PAGE, multiple isoforms of native bovine TAU are converted to a 3 isoform pattern. This is the same 3 isoform apparent pattern produced when the six isoforms of native human TAU are phosphorylated. In-some preparations of bovine TAU, the isoform with the least mobility was less prominent after phosphorylation, essentially creating a pattern of two isoforms which has been observed in some PHF-extracts. The level of phosphorylation and the concomitant conformational changes are approximately equal with partially phosphorylated native TAU and dephosphorylated TAU as substrates.

The bacterially expressed 42 kD human TAU isoform from the clone hTau40 behaves in a way similar to bovine TAU upon PK40 phosphorylation. The gel mobility shift corresponds to about 15 kD of increased apparent size. PK36 was not able to phosphorylate hTau40 to the same extent and consequently induced only a partial mobility shift. The heterogeneous appearance of HTau40 probably reflects the end state of PK36 phosphorylation since the pattern was not altered at threefold higher concentrations of the kinase. Pretreatment with PK40 prior to PK36 phosphorylation produced the same completely shifted band as PK40 alone (not shown).

Treatment of bovine TAU with PK40, but not PK36, also results in phosphorylation of TAU to an extent that yields a phosphorylated-TAU protein that is immunochemically similar to the hyperphosphorylated TAU of PHF-TAU. Dephosphorylated bovine TAU, and native bovine TAU were incubated with 25 pmole/min PK40 or 15 pmole/min PK36 for 18 hours and probed with monoclonal antibodies TAU-1 (SIGMA) (0.15 µg TAU as antigen); SMI33 (0.5 µg TAU as antigen); SMI31 (1 µg TAU as antigen); and SMI34 (2 µg TAU as antigen). TAU-1 does not directly recognize a phosphorylated epitope but PHF-TAU protein treated with phosphates, will bind to TAU-1 (Grundke-Iqbal et al. 1986). SMI-33 also does not directly recognize phosphorylated epitopes but does recognize an epitope on dephosphorylated TAU and on native TAU. This epitope is believed to be the unphosphorylated KSP sequence (Lee et al., 1988), which occurs twice in the sequence of all bovine TAU isoforms (Himmler et al, 1989). Coversely, the SMI-31 epitope is not present in native or dephosphorylated TAU, in agreement with the KSP sites not normally being phosphorylated.

As determined by Western blotting, treatment of native bovine TAU with PK40 completely abolished immunoreactivity towards TAU-1 and SMI-33, but resulted in very strong antibody binding reactions with SMI-31 and SMI-34, both of which detect phosphorylated epitopes. This indicates phosphorylation of the KSP sites of TAU as it occurs in PHF. (The reduction in electrophoetic mobility was also detected on these Western blots. The effect of PK40 treatment on TAU-1 binding is of particular interest since the TAU-1 epitope is masked by phosphorylation in tangles in situ as well as in PHF-TAU on Western blots (Grundke-Iqbal et al. 1986).

In contrast, the only significant immunochemical alteration induced by PK36 treatment of TAU was a strongly reduced SMI 33 activity, the TAU-1 activity being substantially unchanged from diphosphorylated bouine TAU. PK36 is a less efficient phosphorylating kinase of TAU than PK40.

Several kinases have previously been suggested to play a role in the conversion of TAU proteins into PHF-TAU. However, unlike PK40, none confer all the known pathological changes on TAU. Thus, by the criteria of conformational and immunochemical alterations as well as stoichiometry of phosphorylation, PK40, a new member of the ERK-family, can perform abnormal TAU-hyperphosphorylations characteristic of Alzheimer's Disease (AD), Down's Syndrome (DS) and normal aging. PK36 with a partly overlapping site-specificity could not induce TAU-changes to a similar extent.

A variety of immunohistochemical and biochemical studies point to TAU-hyperphosphorylation as an event that precedes tangle formation. PK40 plays a key role in the hyperphosphorylation of TAU. Chronic upregulation of PK40 might cause neurite degeneration and interference with the functional integrity of neurons.

EXAMPLE 10

Uncoupling of oxidative phosphorylation from ATP production by chemical means causes the appearance of immunological epitopes in fibroblast cells from healthy patients, cultured under special conditions. (Blass et al., 1990). This observation is used for the diagnosis of early Alzheimer's disease by linking the appearance of these epitopes to the activity of kinases PK40 and PK36, which are released from inhibition when ATP levels fall, as is the case when oxidative phosphorylation is uncoupled from ATP production. Uncoupling is achieved by the use of an uncoupling reagent, e.g., CCCP (carbonyl cyanide m-chlorophenylhydrazone), or the deprivation of oxygen. The diagnostic test for early neuronal degeneration is applicable for various conditions where neurons degenerate, eq., Alzheimer's disease, Parkinson's disease, Huntington's chorea, normal aging, and brain infarcts.

A diagnostic test for early Alzheimer's disease is described using kinases PK40 and PK36. Primary cultures of skin fibroblasts are obtained from the patient to be tested. These are grown in Dulbecco's modified Eagle's medium containing 0.1 mM dibutyryl cyclic-AMP, 0.1 ug/ml 7S nerve growth factor, 10 ug/ml mixed bovine gangliosides and 5% chick embryo extract. In the presence of an uncoupler of oxidative phosphorylation from ATP production, e.g., CCCP (carbonyl cyanide m-chlorophenyl hydrazone), or with the deprivation of oxygen, the cells show immunological epitopes (Alz-50, PHF-epitopes,SMI-31/SMI-34-positive TAU/neurofilament epitopes), indicating the release from inhibition of kinases PK40 and PK36. Cells from Alzheimer patients show this effect at lower concentrations of uncoupler, compared to normal cells. Thus, cells from patients to be tested are "titrated" with increasing concentrations of uncoupling agent or with decreasing oxygen concentrations. They are distinguished from cells from normal individuals by their lower resistance to the effects of decreasing the ATP concentration.

EXAMPLE 11

Protein Sequencing of PK40

To obtain pure PK40 approximately 150 μg of total protein from the Mono Q FPLC fraction containing enriched kinase was loaded into a 50 mm wide slot and was separated on a 1.5 mm thick 12% SDS-PAGE. The major proteins were made visible by brief immersion into 1M KCl at 4° C. The band corresponding to PK40 was cut out, minced and homogenized in 3 ml of water containing 1 mM DTT with a Mini-Turax. The suspension was sealed into a dialysis bag and shaken with water, 1 mM DTT overnight. The gel fragments were removed by centrifugation and the supernatant was lyophilized.

Peptide Mapping of Kinase

The lyophilisate, containing 20 μg of an apparently homogeneous 40 kD protein on SDS-PAGE. 20 μg kinase was dissolved in 500 μL reduction buffer (6M guangidine hydrochloride/0.5M tris-(hydroxymethyl)-aminomethane pH 8.6). The pH was adjusted to 8.6 with ammonia. 15 μL 1M dithiothetreitol was added. The reduction was performed for 2 h at 52° C. under nitrogen. Then 30 μL μL 1M sodium iodoacetate solution was added and the sample was incubated for 30 min. at room temperature in the dark. Excess reagents were removed by dialysis (cut off 1 kD) against 500 mL 0.5M urea/0.1M $NH_4HCO_3$ pH 8.6 overnight (complete buffer change after 4 h). After dialysis, sequence grade trypsin (Boehringer Mannheim) was added in the ratio 1:20. The protein was cleaved for 18 h at 37° C. The solution was then concentrated to about 250 μL. The reaction was stopped by cooling to 4° C. After concentration the peptides were separated HPLC.

Separation of Tryptic Peptides by HPLC

A sample was injected onto an HP 1090 HPLC-system equipped with an Nucleosil RP-18 HPLC-column (CS-Chromatographie Service) 250 mm×4.6 mm; 5 μmaterial; 300 Angstrom), and samples were collected at 0.7 ml/min., 40 C. with 0.1% TFA and a gradient from 0 to 70% acetonitrile. The single peptides were collected as 0.5 min. fractions using a fraction collector from LKB/Pharmacia Superrac model 2211. Elution of peptides was monitored at 210, 280 and 295 nm and 0.35 ml fractions were collected. The single fractions were lyophilized after separation.

Chromatographic conditions: flow 0.7 mL/min, column temperature 40° C., detection 210 nm, 280 nm and 295 nm, solvent A 0.1% TFA,,solvent B 60% acetonitril/0.1% TFA, gradient 5 min 0% B, 120 min 70% B, 125 min 100% B, 130 min 0% B, 140 min 0% B.

All chemicals used were of biochemical or analytical quality and were purchased from Bio-Rad (D-8000 Munich), Pharacia/LKB (D-7800 Freiburg), Merck (D-6100 Darmstadt), Serva (D-6900 Heidelberg), Applied Biosystems (sequencer chemicals; D-6108) Weiterstadt or Pierce (PTH-amino acid standard; Rockford, Ill. 61105 U.S.A.), Boehringer (D-6800 Mannheim) for sequence grade trypsin.

The dialysis tube was from Reichelt Chemietechnik (D-6900 Heidelberg).

The gas phase protein sequencer model 470A was purchased from Applied Biosystems. A slightly modified standard sequencer program was used. The sequencer is described in detail in the respective instrument manual.

For detection of phenylthiohydantion amino acids (PTH-aa) a HPLC system from Hewlett Packard PH 1082 and an autosampler from Waters (D-5090 Leverkusen) WISP 7208 equipped with a Kontron (D-4000 Dusseldorf) datasystem MT 450 were used. The HPLC-columns used for PTH-detection (250 mm×4.6 mm) filled with Superspher™ material from Merck were purchased from CS-Chromatographie Service (D-5163 Langerwehe).

Peptide maps were run on an HPLC-system from Hewlett Packard HP 1090 equipped with a diode array detector HP1040A and a chemstation with the integration software. The-HPLC-column for peptide mapping was purchased from CS-Chromatrographie Service (Nucleiosil RP-19; 250 mm×4.6 mm; 5 μmaterial; 300 Angstrom).

N-Terminal sequence analysis

N-terminal sequence analysis was performed using the gas phase protein sequencer 470A from Applied Biosystems. The standard sequencer program was used with a slight modification instead of 20% trifluoro acetic acid (TFA) 1M methanolic HCl was taken for conversion of PTH-amino acids. 50–100 pmol of kinase peptides were used for sequencing.

For the identification of PTH-amino acids a HPLC-system based on a Merck Superspher™ column was used (Lottspeich F. 1985. "Microscale isocratic separation of phenylthiohydantoin amino acid derivatives", *J. Chromatography* 326: 321–327). The system was run isocratically.

Conditions: flow 1.5 mL/min, detection 269 nm, oven temperature 61° C., mobile phase 68.5% 10 mM sodium acetate, pH 4.9/31.5% acetonitril supplemented with 5 mL dichloromethane per L.

The calibration was performed with a 25 pmol standard of all PTH-amino acids before each sequencer run.

The purified tryptic digests are given as Sequence I.D. Nos. 1–15.

The sequences of these tryptic digests (Seq. I.D. Nos. 1–15) were compared to the known amino acid sequences of the ERK1 and ERK2 proteins derived from rat brain cDNA clones (Boulton et al., 1991). Sequence I.D. Nos. 3–15 matched very closely the ERK-kinase family proteins. ERK's have the highest homology (about 40%) to cell cycle-associated cdc2 kinase and thus PK40 can be considered to be a member of the cell cycle-associated ERK kinase family. Sequence I.D. Number 6 contains the consenses site of serine/threonine kinases for nucleotide binding, Gly Glu Gly Ala Tyr Gly (Hanks et al., 1988).

Sequence I.D. Numbers 1 and 2 were not homologous to any of the ERK proteins.

EXAMPLE 12

A cloning procedure for cDNAs encoding kinases PK40 and PK36 is described. A radiolabeled synthetic oligonucleotide hybridization probe corresponding to the most unique codons of the peptide sequence for each of the PK40 and PK36 kinases is prepared.

Specifically, probes corresponding to Sequence I.D. Numbers 1 and 2 are most suitable for the cloning procedure for cDNA encoding PK40.

The oligonucleotide probes (e.g. Sequence I.D. Nos. 1 and 2) for PK40 and oligonucleotide probes for PK36 are used to screen lambda gt11 cDNA libraries prepared from poly(A)$^{30}$ RNA from human fetal brain cells, commercially available from a variety of sources. Hybridization conditions are as described by Cate et al. (1986), except that the final wash in tetramethyl ammonium chloride is omitted. DNA inserts from positive plaques are subcloned directly into the plasmid vector pBlue-script SKM13+ (Stratagene, Inc. San Diego, Calif.). Positive plasmid subclones are identified by colony hybridization, with the use of the same oligonucleotide hybridization probe. Minipreparations of plasmid DNA are prepared from positive colonies.

The nucleotide sequence immediately upstream from the oligonucleotide binding site is determined by double strand sequencing (Chen and Seeburg, 1985), using $^{32}$P end-labeled oligonucleotide as sequencing primer and non-radioactive nucleotides in the extension reactions. Subclones whose codon order upstream from the priming site match the known amino acid sequence are sequenced in their entirety by the dideoxy chain termination method, with either the Klenow fragment of *Escherichia coli* DNA polymerase I or modified bacteriophage T7 DNA polymerase (Sequenase; United States Biochemicals) in the extension reactions. Subclones are sequenced from their termini, from both directions from a set of restriction sites. Clones are obtained whose codon order matches the amino acid sequence of each of the kinases. A full-length CDNA sequence is assembled from the overlapping partial clones for each of the kinases.

REFERENCES

Blanchard BJ, Ingram VM (1989) Age-related neurofilament phosphorylation in normal human brains. Neurobiol of Aging 10:253–258.

Blass JP, Baker AC, Li-wen K, Black RS (1990) Induction of Alzheimer Antigens by an Uncoupler of Oxidative Phosphorylation; Arch.Neurol. 47:864–868.

Boulton, T. G., Gregory, J. S. and Cobb, M. H. (1991) Purification and properties of ERK1, an insulin-stimulated MAP2 protein kinase, Biochem. 30: 278–286.

Cate R, Mattaliano R, Hession C, Tizard R, Farber N, Cheung A, Ninfa E, Frey A, Gash D, Chow E, Fisher R, Bertonis J, Torres G, Wallner B, Ramachandran F, Ragin R, Manganaro T, MacLaughlin D, Donahoe P (1986). Cell 45:685–698.

Chen E, Seeburg P (1985). DNA 4:165–170.

Crews, C. M., Alessandrini, P. A., and Erikson, R. L. (1991) Mouse ERK-1 gene product is a serine/threonine protein kinase that has the potential to phosphorylate tyrosine. Proc. Natl. Acad. Sci. USA 88: 8845–8849.

Dixon M, Webb ED (1979) The Enzymes, pp 60–62, Academic Press, New York.

Goedert M, Spillantini MG, Jakes R, Rutherford D, Crowther RA (1989) Multiple isoforms of human microtubule-associated protein TAU: Sequences and localization in neurofibrillary tangles of Alzheimer's disease. Neuron 3:519–526.

Goedert M, Spillantini MG, Cairnns NJ, Crowther RA (1992) TAU Proteins of Alzheimer's Paired Heilical Filaments: Abnormal Phosphorylation of All Six Brain Isoforms, Neuron 8:159–168.

Grundke-Iqbal I, Iqbal K, Tung Y-C, Quinlan M, Wisniewski HM, Binder LI (1986) Abnormal phosphorylation of the microtubule-associated protein (TAU) in Alzheimer cytoskeletal pathology. Proc Natl Acad Sci USA 83:4913–4917.

Hagestedt T, Lichtenberg B, Wille H, Mandelkow E-M, Mandelkow E (1989) Tau protein becomes long and stiff upon phosphorylation: Correlation between paracrystalline structure and degree of phosphorylation. J Cell Biol 109:1643–1651.

Hanks, S. K., Quinn, A. M., and Hunter, T., (1988) The protein kinase family: conserved features and deduced phylogeny of the catalytic domains, Science 241: 42–52.

Himmler A, Drechsel D, Kirschner MW, Martin DW (1989) Tau consists of a set or proteins with repeated C-terminal microtubule-binding domains and variable N-terminal domains. Mol Cell Biol 9:1381–1388.

Hirokawa N. Glicksman MA, Willard MB (1984) Organization of mammalian neurofilament polypeptides within the neuronal cytoskeleton. J Cell Biol 98:1523–1536.

Hoffman PN, Cleveland DW, Griffin JW, Lander PW,

Cowan NJ, Price DL (1987) Neurofilament gene expression: a major determinant of axonal caliber. Proc Natl Acad Sci USA 84:3472–76.

Iqbal K, Grundke-Iqbal I, Smith AJ, George L, Tung Y-C, Zaidi T (1989) Identification and localization of a t peptide to paired helical filaments of Alzheimer disease. Proc Natl Acad Sci USA 86:5646–5650.

Karlsson J-E, Rosengren LE, Haglid KG (1987) A rapid HPLC method to separate the triplet proteins of neurofilament. J Neurochem 49:1375–1378.

Kaufmann E, Geisler N, Weber K (1984) SDS-PAGE strongly overestimates the molecular mass of the neurofilament proteins. FEBS Lett 170:81–84. Kondo J, Honda T, Mori H, Hamada Y, Miura R, Ogawara M, Ihara Y (1988) The carboxyl third of TAU is tightly bound to paired helical filaments. Neuron 1:827–834.

Kosik KS, Joachim CL, Selkoe DJ (1986) Microtubule-associated protein TAU (t) is a major antigenic component of paired helical filaments in Alzheimer disease. Proc Natl Acad Sci USA 83:4044–4048.

Laemmli UK (1970) Cleavage of structural proteins during the assembly of the head of bacteriophage T4. Nature 227:680–685.

Lees JF, Shneidman PS, Skuntz SF, Carden MJ, Lazzarini RA (1988) The structure and organization of the human heavy neurofilament subunit (NF-H) and the gene encoding it. EMBO J 7:1947–1955.

Leterrier J-F, Liem RKH, Shelanski ML (1981) Preferential phosphorylation of the 150,000 molecular weight component of neurofilaments by a cyclic AMP-dependent, microtubule associated protein kinase. J Cell Biol 90:755–760.

Lindwall G, Cole RD (1984) Phosphorylation affects the ability of TAU protein to promote microtubule assembly. J Biol Chem 259:5301–5305.

Matus A. (1988) Neurofilament protein phosphorylation–where, when and why. TINS 11:291–292.

Milstein, Kohler (1975). Nature 256:495–497.

Minami Y, Sakai H (1983) Network formation by neurofilament-induced polymerization of tubulin: 200 K subunit of neurofilament triplet promotes nucleation of tubulin. J Biochem 94:2023–2033.

Minami Y, Sakai H (1985) Dephosphorylation suppresses the activity of neurofilament to promote tublin polymerization. FEBS Lett 185:239–242.

Myers MW, Lazzarini RA, Lee VM-Y, Schlaepfer WW, Nelson DL (1987) The human mid-size neurofilament subunit: a repeated protein sequence and the relationship of its gene to the intermediate filament gene family. EMBO J 6:617–1626.

Napolitano EW, Chin SSM, Colman DR, Liem RKH (1987) Complete amino acid sequence and in vitro expression of rat NF-M, the middle molecular weight neurofilament protein. J Neurosci 7:2590–2599.

Nukina N, Kosik KS, Selkoe DJ (1987) Recognition of Alzheimer paired helical filaments by monoclonal neurofilament antibodies is due to crossreaction with TAU protein. Proc Natl Acad Sci USA 84:3415–3419.

O'Farrell PH, (1975) High Resolution 2 Diminsional Electrophoses of Proteins. 5 Biol Chem Vol 250, p. 4007–22.

Pant HC, Shecket G, Gainer H, Lasek RJ (1978) Neurofilament protein is phosphorylated in the squid giant axon. J Cell Biol 78:R23-R27.

Pepinski, R, Sinclair L, Browning J, Mattaliano R, Smart J, Chow E, Falbel T, Ribolini A, Garvin J, Wallner B (1986). J Biol Chem 261;4239–4246.

Pleasure SJ, Selzer ME, Lee VM-Y (1989) Lamprey neurofilaments combine in one subunit the features of each mammalian NF triplet protein but are highly phosphorylated only in large axons. J Neurosci 9:698–709.

Pleasure SJ, Lee VM-Y, Nelson DL (1990) Site-specific phosphorylation of the middle molecular weight human neurofilament protein in transfected non-neuronal cells. J Neurosci 10:2428–2437.

Rasool CG, Selkoe DJ (1984) Alzheimer's disease: exposure of neurofilament immunoreactivity in SDS-insoluble pairedhelical filaments. Brain Res 322:194–198.

Runge, Ms, El-Maghrabi MR, Claus TH, Pilkis SJ, Williams RC (1981) A MAP-2-stimulated protein kinase activity associated with neurofilaments. Biochemistry 20:175–180.

Shecket G, Lasek RJ (1982) Neurofilament protein phosphorylation. J Biol Chem 257:4788–4795.

Steiner L, Pardo A, Margolies M (1979). Biochemistry 18:4068–4073.

Sternberger NH, Sternberger LA (1983) Monoclonal antibodies distinguish phosphorylated and nonphosphorylated forms of neurofilaments in situ. Proc Natl Acad Sci USA 80:6126–6130.

Sternberger NH, Sternberger LA, Ulrich J (1985) Aberrant neurofilament phosphorylation in Alzheimer disease. Proc Natl Acad Sci USA 82:4274–4276.

Tokutake S, Hutchison SB, Pachter JS, Liem RKH (1983) A batchwise purification procedure of neurofilament proteins. Anal Biochem 135:102–105.

Tokutake S (1984) Complete separation of the triplet components of neurofilament by DE-52 column chromatography depends upon urea concentration. Anal Biochem 140:203–207.

Toru-Delbauffe D, Pierre M (1983) A rat brain proteir. kinase phosphorylating specifically neurofilaments. FEBS Letters 162:230–234.

Ueda K, Masliah E, Saitoh T, Bakalis SL, Scoble H, Kosik KS (1990) Alz-50 recognizes a phosphorylated epitope of TAU protein. J Neurosci 10:3295–3304.

Wible BA, Smith KE, Angelides KJ (1989) Resolution and purification of a neurofilament-specific kinase. Proc Natl Acad Sci USA 86:720–724.

Wischik CM, Novak M, Edwards PC, Klug A, Tichelaar W. Crowther RA (1988) Structural characterization of the core of the paired helical filament of Alzheimer disease (1988). Proc Natl Acad Sci USA 85:4884–4888.

Wong J. Hutchison SB, Liem RKH (1984) An isoelectric variant of the 150,000-Dalton neurofilament polypeptide. J Biol Chem 259:10867–10874.

Wood, JG, Mirra SS, Pollock NJ, Binder LI (1986) Neurofibrillary tangles of Alzheimer disease share antigenic determinants with the axonal microtubule-associated protein TAU (t). Proc. Natl. Acad. Sci. USA 83:4040–4043.

We claim:

1. A method for inhibiting abnormal tau hyperphosphorylation activity in a cell comprising:

contacting a cell with an inhibitor that binds to an ATP binding site of PK40 and inhibits the phosphorylating activity of PK40, in an amount sufficient to inhibit said phosphorylating activity of PK40 which is characteristic of abnormal tau hyperphosphorylation in Alzheimer's Disease.

2. The method claim 1, wherein the inhibitor is ATP or an analog of ATP.

3. The method of claim 2, wherein the inhibitor is an analog of ATP.

* * * * *

```
SEQUENCE LISTING (1) GENERAL INFORMATION:

(iii) NUMBER OF SEQUENCES:   15

(2) INFORMATION FOR SEQ ID NO: 1:

(i) SEQUENCE CHARACTERISTICS:
        (A) LENGTH: 14 amino acids
        (B) TYPE: amino acid
        (D) TOPOLOGY: linear
```

(ii) MOLECULE TYPE: peptide (xi) SEQUENCE DESCRIPTION: SEQ ID NO: 1:

Gly Gln Val Phe Asp Val Gly Pro Val Gly Leu Ala Gly Pro
            1               5                  10

(2) INFORMATION FOR SEQ ID NO: 2:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO: 2:

Gln Thr Gly Pro Ile Gly Pro His Gly Pro Gln Gly
            1               5                  10

(2) INFORMATION FOR SEQ ID NO: 3:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO: 3:

Xaa Ile Glu Val Glu Gln Ala Leu Ala Thr Pro Tyr Xaa Glu
            1               5                  10

(2) INFORMATION FOR SEQ ID NO: 4:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO: 4:

Xaa Ile Glu Val Glu Gln Ala Leu Ala His Pro Tyr Xaa Glu
            1               5                  10

(2) INFORMATION FOR SEQ ID NO: 5:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO: 5:

Ile Glu Val Glu Gln Ala Leu Ala His Pro Tyr Xaa Glu Gln Tyr
            1               5                  10                  15

(2) INFORMATION FOR SEQ ID NO: 6:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO: 6:

Tyr Thr Asn Leu Ser Tyr Ile Gly Glu Gly Ala Xaa Gly Met Val

```
                         1               5              10              15
```

(2) INFORMATION FOR SEQ ID NO: 7:

(i) SEQUENCE CHARACTERISTICS:
        (A) LENGTH: 14 amino acids
        (B) TYPE: amino acid
        (D) TOPOLOGY: linear     (ii) MOLECULE TYPE: peptide     (xi) SEQUENCE DESCRIPTION: SEQ ID NO: 7:

```
        Asp Val Tyr Ile Val Gln Asp Leu Met Glu Thr Asp Leu Tyr
        1               5                   10
```

(2) INFORMATION FOR SEQ ID NO: 8:

(i) SEQUENCE CHARACTERISTICS:
        (A) LENGTH: 8 amino acids
        (B) TYPE: amino acid
        (D) TOPOLOGY: linear     (ii) MOLECULE TYPE: peptide     (xi) SEQUENCE DESCRIPTION: SEQ ID NO: 8:

```
        Asn Tyr Leu Leu Ser Leu Pro Xaa
        1               5
```

(2) INFORMATION FOR SEQ ID NO: 9:

(i) SEQUENCE CHARACTERISTICS:
        (A) LENGTH: 9 amino acids
        (B) TYPE: amino acid
        (D) TOPOLOGY: linear     (ii) MOLECULE TYPE: peptide     (xi) SEQUENCE DESCRIPTION: SEQ ID NO: 9:

```
        Glu Leu Ile Phe Glu Glu Thr Ala Xaa
        1               5
```

(2) INFORMATION FOR SEQ ID NO: 10:

(i) SEQUENCE CHARACTERISTICS:
        (A) LENGTH: 8 amino acids
        (B) TYPE: amino acid
        (D) TOPOLOGY: linear     (ii) MOLECULE TYPE: peptide     (xi) SEQUENCE DESCRIPTION: SEQ ID NO: 10:

```
        Met Leu Thr Phe Asn Pro Xaa Lys
        1               5
```

(2) INFORMATION FOR SEQ ID NO: 11:

(i) SEQUENCE CHARACTERISTICS:
        (A) LENGTH: 8 amino acids
        (B) TYPE: amino acid
        (D) TOPOLOGY: linear     (ii) MOLECULE TYPE: peptide     (xi) SEQUENCE DESCRIPTION: SEQ ID NO: 11:

```
        Ile Cys Asp Phe Gly Leu Ala Xaa
```

(2) INFORMATION FOR SEQ ID NO: 12:

(i) SEQUENCE CHARACTERISTICS:
        (A) LENGTH: 7 amino acids
        (B) TYPE: amino acid
        (D) TOPOLOGY: linear     (ii) MOLECULE TYPE: peptide     (xi) SEQUENCE DESCRIPTION: SEQ ID NO: 12:

Ala Leu Asp Leu Leu Asp Xaa
        1           5

(2) INFORMATION FOR SEQ ID NO: 13:

(i) SEQUENCE CHARACTERISTICS:
        (A) LENGTH: 7 amino acids
        (B) TYPE: amino acid
        (D) TOPOLOGY: linear     (ii) MOLECULE TYPE: peptide     (xi) SEQUENCE DESCRIPTION: SEQ ID NO: 13:

Asp Val Tyr Ile Val Gln Asp
        1           5

(2) INFORMATION FOR SEQ ID NO: 14:

(i) SEQUENCE CHARACTERISTICS:
        (A) LENGTH: 6 amino acids
        (B) TYPE: amino acid
        (D) TOPOLOGY: linear     (ii) MOLECULE TYPE: peptide     (xi) SEQUENCE DESCRIPTION: SEQ ID NO: 14:

Ala Pro Glu Ile Met Leu
        1           5

(2) INFORMATION FOR SEQ ID NO: 15:

(i) SEQUENCE CHARACTERISTICS:
        (A) LENGTH: 6 amino acids
        (B) TYPE: amino acid
        (D) TOPOLOGY: linear     (ii) MOLECULE TYPE: peptide     (xi) SEQUENCE DESCRIPTION: SEQ ID NO: 15:

Ser Ile Asp Ile Xaa Ser
        1           5